United States Patent
Oh et al.

(10) Patent No.: US 7,846,702 B2
(45) Date of Patent: Dec. 7, 2010

(54) METHOD FOR PREPARING XYLITOL WITH HIGH YIELD USING RECYCLING MICROORGANISM

(75) Inventors: Deok-kun Oh, Gyeonggi-do (KR); Taek-bum Kim, Chungcheongnam-do (KR); Jung-hoon Kim, Seoul (KR); Seong-bo Kim, Seoul (KR); Seung-won Park, Gyeonggi-do (KR); Soon-chul Kim, Incheon (KR)

(73) Assignee: CJ Cheiljedang Corporation, Seoul (KR)

( * ) Notice: Subject to any disclaimer, the term of this patent is extended or adjusted under 35 U.S.C. 154(b) by 169 days.

(21) Appl. No.: 12/188,466

(22) Filed: Aug. 8, 2008

(65) Prior Publication Data
US 2009/0197313 A1 Aug. 6, 2009

Related U.S. Application Data

(62) Division of application No. 10/582,148, filed as application No. PCT/KR2004/003024 on Nov. 22, 2004, now Pat. No. 7,427,500.

(30) Foreign Application Priority Data
Dec. 8, 2003 (KR) ............ 10-2003-0088489

(51) Int. Cl.
C12P 7/18 (2006.01)
C12N 1/16 (2006.01)
(52) U.S. Cl. ............ 435/158; 435/254.22; 435/255.4
(58) Field of Classification Search ............ None
See application file for complete search history.

(56) References Cited

U.S. PATENT DOCUMENTS
2004/0014185 A1* 1/2004 Ojamo et al. ............ 435/158

FOREIGN PATENT DOCUMENTS
| JP | 12-093188 | 4/2000 |
| KR | 99-65347 | 8/1999 |
| KR | 99-86862 | 12/1999 |
| KR | 00-76625 | 12/2000 |

OTHER PUBLICATIONS

Choi et al "Production of xylitol in recycle fermentations of *Candida tropicalis*" Biotechnology Letters 2000 V 22, pp. 1625-1628.*
Kim et al., "Increased Xylitol Production Rate During Long-term Cell Recycle Fermentation of *Candida tropicalis*," Biotechnol Lett, vol. 26, No. 8, pp. 623-627 (2004).
Baishan et al., "Using Genetic Algorithms Coupling Neural Networks in a study of Xylitol Production: Medium Optimisation", J. Process Biochemistry, 38:979-985 (2003).

* cited by examiner

Primary Examiner—Herbert J. Lilling
(74) Attorney, Agent, or Firm—Occhiuti Rohlicek & Tsao LLP

(57) ABSTRACT

Provided is a process for continuously producing xylitol in high yield and productivity using a vacuum microfiltration bioreactor containing a fermentation medium for a strain of the genus *Candida*, which includes: 5 300 g/l of xylose, 1 10 g/l of urea, 1 10 g/l of potassium diphosphate, 0.01 1 g/l of magnesium sulfate, 0.1-10 mg/l of $MnSO_4 04H_2O$, 0.1 10 mg/l of $CoCl_2$-$6H_2O$, 0.1 10 mg/l of $NaMoO_4$-$2H_2O$, 0.1 10 mg/l of $ZnSO_4$-$7H_2O$, 0.1 10 mg/l of $AlCl_3$-$6H_2O$, 0.1 10 mg/l of $CuCl_2$-$2H_2O$, 0.01-5 mg/l of $H_3BO_3$, 1-100 mg/l of $FeSO_4$ $7H_2O$, 0.1-10 mg/l of ascorbic acid, 1-100 mg/l of biotin, 1-100 mg of choline, 1-200 mg/l of folic acid, 1-100 mg/l of inositol, 1-100 mg/l of nicotinic acid, 0.1-10 mg/l of p-aminobezoic acid, 1-100 mg/l of pantothernic acid, 0.1-10 mg/l of pyridoxine, 10-1,000 mg/l of riboflavin, and 1-100 mg/l of thiamine.

17 Claims, 4 Drawing Sheets

[FIG. 1]
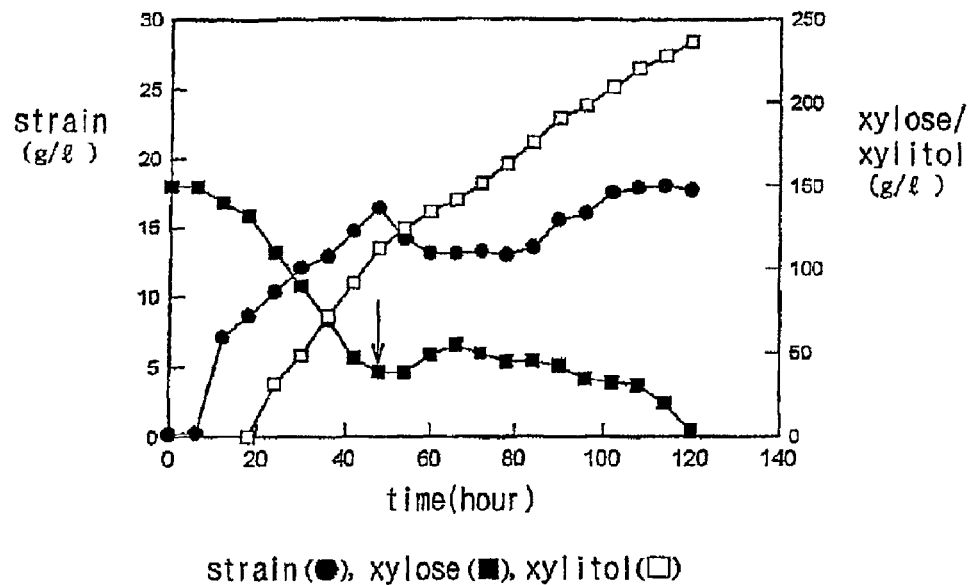
strain(●), xylose(■), xylitol(□)
[FIG. 2]
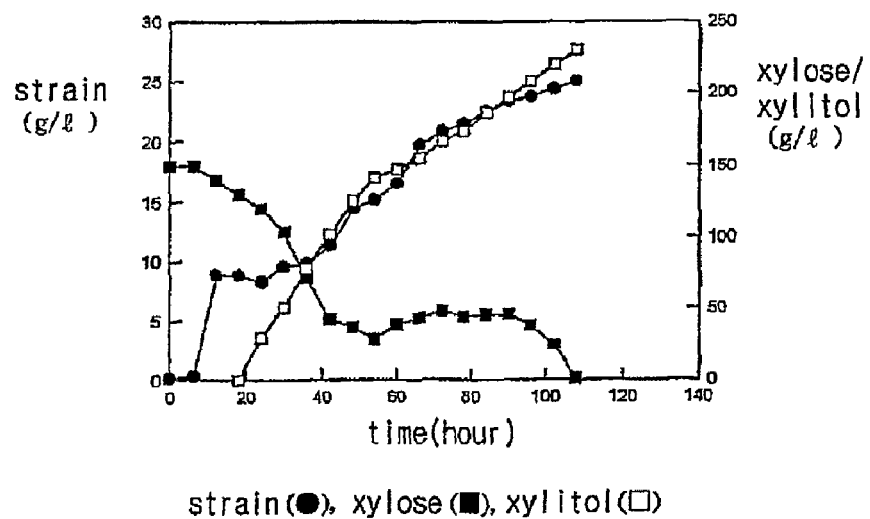
strain(●), xylose(■), xylitol(□)

[FIG. 3]
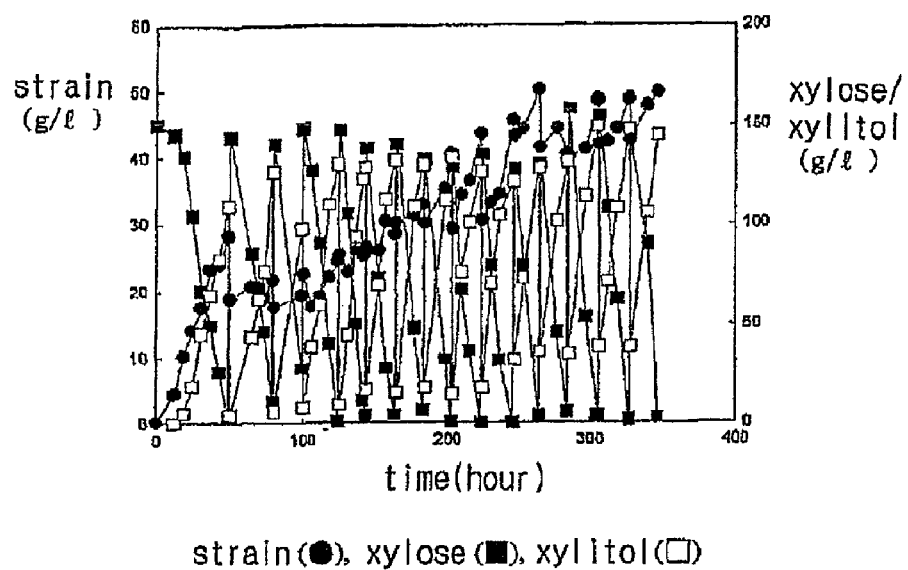
strain(●), xylose(■), xylitol(□)
[FIG. 4]
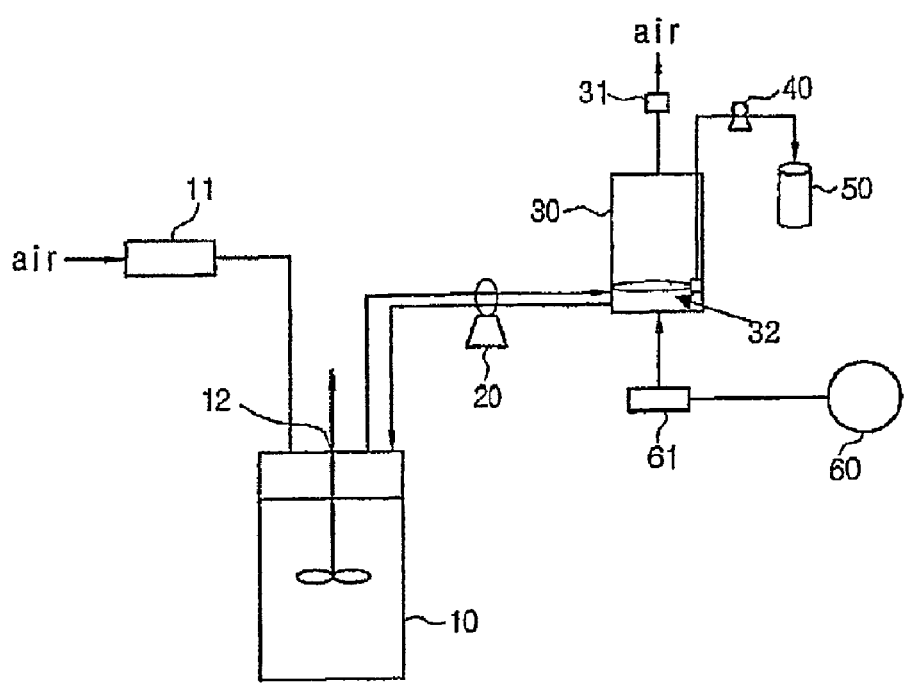

[FIG. 5]
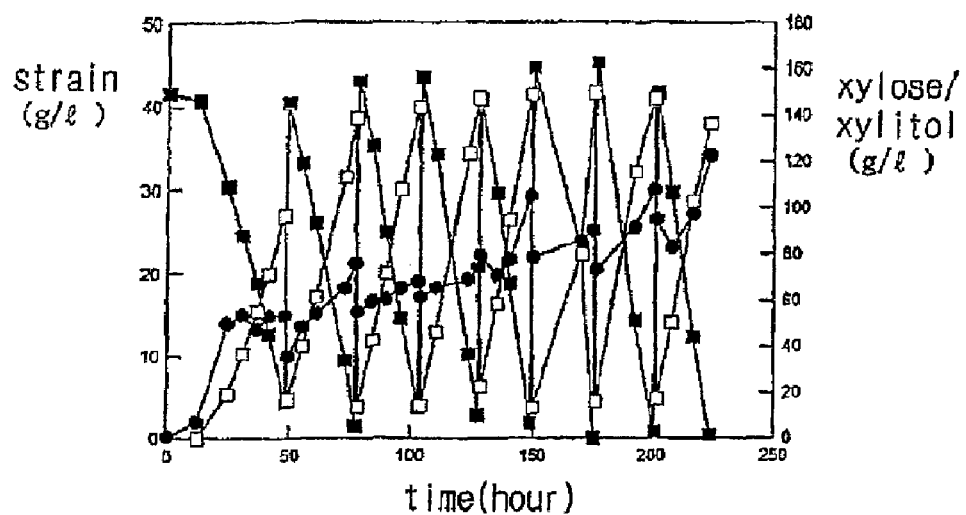
[FIG. 6]
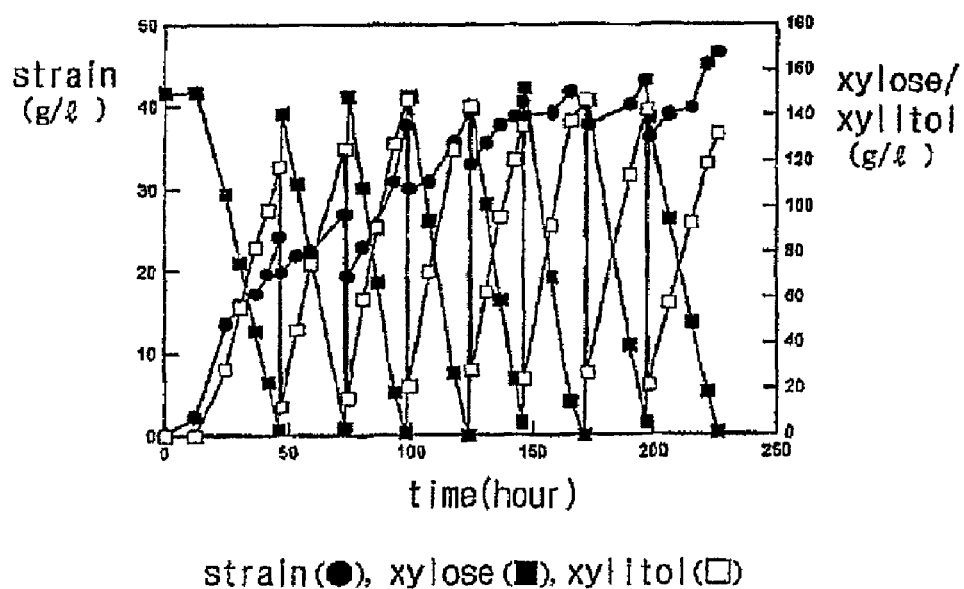
strain(●), xylose(■), xylitol(□)

[FIG. 7]
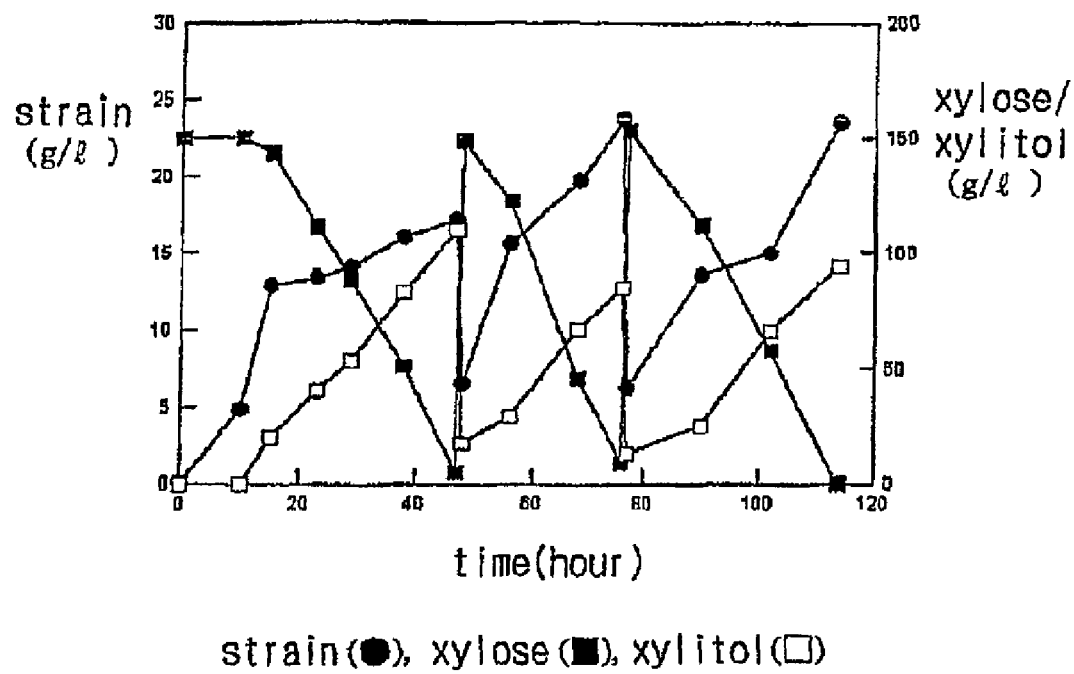
strain(●), xylose(■), xylitol(□)

METHOD FOR PREPARING XYLITOL WITH HIGH YIELD USING RECYCLING MICROORGANISM

CROSS-REFERENCE TO RELATED APPLICATION

This application is a divisional of U.S. application Ser. No. 10/582,148, filed Jun. 7, 2006, now U.S. Pat. No. 7,427,500 which is a U.S. national phase application of PCT/KR2004/003024, filed Nov. 22, 2004, which claims priority to Korea application number 10-2003-0088489, filed Dec. 8, 2003

TECHNICAL FIELD

The present invention relates to a process for continuously producing xylitol from xylose with high productivity by recycling culture of a concentrated strain in a vacuum microfiltration bioreactor.

BACKGROUND ART

Xylitol was first reported by a chemist Emil Fisher in 1981 and is a five-carbon sugar alcohol that has been used as a sweetener since 1960. Xylitol is found in small quantities in natural plants such as fruits, vegetables, and mushrooms, and is an intermediate of mammalian carbohydrate metabolism. Furthermore, because of its sweetness equivalent to sucrose and its negative heat of dissolution, xylitol imparts a cool and refreshing sensation in the oral cavity. Therefore, xylitol is used as a material for sugar-free confectionery products. In particular, since it does not require insulin to be metabolized after its intake, xylitol can be used as a sugar substitute for diabetic patients.

Xylitol can prevent cavities by inhibiting the growth of *Streptococcus mutans* which is responsible for tooth decay, and thus, is used as a material of toothpaste. Furthermore, xylitol does not participate in the Maillard reaction, and is a monosaccharide and thus cannot undergo inversion unlike sucrose. Therefore, xylitol has no risk of degeneration even when used at an acidic environment. Still furthermore, xylitol has a low boiling point of 95° C., and thus, can reach its boiling point with no denaturalization. Therefore, when used as a sugar-coating, xylitol is not particularly required to be dissolved in water.

Xylitol is produced on an industrial scale by chemical reduction of a hydrolysate of hemicellulose taken from plants such as white birch trees, corn cobs, etc. or by biological conversion of the hydrolysate to xylitol using a microbial strain. With respect to the chemical production method, however, separation and purification of xylose or xylitol from other hydrolysates derived from hemicellulose fractions are difficult and the yield of xylose or xylitol is as low as 50-60%. Furthermore, there arise problems such as a risk of high-temperature and high-pressure reaction and waste disposal due to use of alkali. To solve these problems, industrial-scale production of xylitol using a microbial strain has been reported. Xylitol production using a microbial strain is cost-effective, and enables selective conversion of xylose to xylitol, thereby facilitating separation and purification of xylitol. However, there are disadvantages in that xylitol productivity is as low as 2.0-3.0 g/l-h and a microbial strain can be used only once. For this reason, once culturing is finished, conventional xylitol production techniques involve preparative procedures for re-culturing, such as washing and sterilization, thereby leading to an increase of production cost.

In xylitol production using a strain of the genus *Candida*, xylose or hemicellulose hydrolysate comprised mainly of xylose is used as a carbon source. As a nitrogen source, there is used a complex nitrogen source containing various vitamins such as yeast extract, malt extract, soybean meal, etc. This is because strains of the genus *Candida* are relatively complex auxotrophs, thereby scarcely producing xylitol in a chemical synthetic medium. In this respect, use of an expensive complex medium becomes a contributing factor to the increased cost of xylitol.

Therefore, to solve the problems of the above-described xylitol production using a microbial strain, the present inventors developed a process for producing xylitol from a culture of a microbial strain cultured in a chemically defined medium. According to this process, the microbial strain is concentrated and recycled after isolated from the culture. This xylitol production process can be applied to an automated continuous culture system, thereby leading to reduction of a production cost due to a simplified culture procedure and continuous production of xylitol. The present inventors thus completed the present invention.

DISCLOSURE OF INVENTION

In view of these problems, the present invention provides a chemically defined medium for the cultivation of a strain of the genus *Candida* that produces xylitol.

The present invention also provides a process for producing xylitol in high yield using a microbial strain, in which the strain and a culture filtrate are separated from a culture and the strain is concentrated for recycling.

According to an aspect of the present invention, there is provided a chemically defined medium for fermentation culture of a strain of the genus *Candida*, which includes 5-300 g/l of xylose, 1-10 g/l of urea, 1-10 g/l of potassium diphosphate, 0.01-1 g/l of magnesium sulfate, 0.1-10 mg/l of $MnSO_4.4H_2O$, 0.1-10 mg/l of $CoCl_2.6H_2O$, 0.1-10 mg/l of $NaMoO_4.2H_2O$, 0.1-10 mg/l of $ZnSO_4.7H_2O$, 0.1-10 mg/l of $AlCl_3.6H_2O$, 0.1-10 mg/l of $CuCl_2.2H_2O$, 0.01-5 mg/l of $H_3BO_3$, 1-100 mg/l of $FeSO_4.7H_2O$, 0.1-10 mg/l of ascorbic acid, 1-100 mg/l of biotin, 1-100 mg/l of choline, and 0.1-10 mg/l of pyridoxine.

According to another aspect of the present invention, there is provided a process for producing xylitol in high yield by recycling culture of a strain of the genus *Candida*, which includes: inoculating the strain in a xylose-containing medium and culturing the strain in the xylose-containing medium in a bioreactor; releasing a culture from the bioreactor and introducing a fresh xylose-containing medium to the bioreactor; separating the strain and a culture filtrate from the culture; and recycling the strain to the bioreactor and recovering xylitol from the culture filtrate.

The strain of the genus *Candida* may be *Candida tropicalis* or its mutant strain.

The xylose-containing medium used in the present invention may be the above-described chemically defined medium (simply referred to as "chemical medium", hereinafter) or a complex medium containing a complex nitrogen source such as yeast extract, malt extract, and soybean meal. However, it is preferable to use the chemical medium with a view to cost effectiveness such as production cost. At this time, xylose or hemicellulose hydrolysate comprised mainly of xylose may be used as a carbon source.

To facilitate growth of the strain, the chemical medium may be supplemented with 1-200 mg/l of folic acid, 1-100 mg/l of inositol, 1-100 mg/l of nicotinic acid, 0.1-10 mg/l of p-aminobezoic acid, 1-100 mg/l of pantothenic acid, 10-1,000 mg/l of riboflavin, and 1-100 mg/l of thiamine.

In the production process of the present invention, the strain is cultured by a fed-batch culture method or a batch culture method.

With respect to fed-batch culture of the strain, it is preferable that the medium is gradually supplemented with xylose used as a carbon source so that the concentration of xylose is maintained at the level of 40-50g/l (based on the medium). At this time, stirring is performed at a speed of 400-600 rpm.

Meanwhile, the released culture is separated into the strain and the culture filtrate by a vacuum microfiltration system or a centrifuge. In particular, to utilize an automated system, it is preferable to use a vacuum microfiltration system. The vacuum microfiltration system may be separately attached to the bioreactor or installed in the bioreactor.

The strain separated from the culture is concentrated and recycled. Preferably, the strain is concentrated to a density of 10-100 g/l of the medium.

Hereinafter, preferable embodiments of a process for producing xylitol in high yield according to the present invention will be described in more detail with reference to the accompanying drawings.

However, these embodiments are provided only for illustrations and thus the present invention is not limited to or by them.

First, an overall production process of the present invention will be simply described with reference to FIG. 4 illustrating a bioreactor equipped with a vacuum microfiltration system.

Referring to FIG. 4, a microbial strain is cultured in a bioreactor 10. The resultant culture is transferred to a microfiltration system 30 by a peristaltic pump 20. At this time, to facilitate filtration, air is forcedly supplied into the microfiltration system 30 via a lower air inlet (not shown). During the air supply, when a suction pump 40 connected to hollow fiber members (not shown) fixed on both sides of the microfiltration system 30 is operated, a pressure difference by pressure drop is caused in the microfiltration system 30. Due to the pressure difference, the culture is allowed to pass through the hollow fiber members fixed on both sides of the microfiltration system 30. At this time, the strain, which has not passed through the hollow fiber members, is concentrated on the lower portions of the hollow fiber members, and then recycled to the bioreactor 10 by the peristaltic pump 20 for re-culturing. A culture filtrate, which has passed through the hollow fiber members, is transferred to a broth tank 50 by the suction pump 40, to thereby yield xylitol by a common purification process.

Meanwhile, when filtration in the microfiltration system 30 is completed, a little fresh medium is added to the hollow fiber members in an opposite direction to the flow direction of the culture to detach the strain from the hollow fiber members. Then, the strain is recycled to the bioreactor 10 by the peristaltic pump 20 and the hollow fiber members are restored to their former conditions by air supply. Thereafter, culturing is again performed in the bioreactor 10 containing a fresh medium. For reference, the numeral 11

A culture state is determined using a substrate (xylose) concentration, a product (xylitol) concentration, and strain concentration converted to dry weight. At this time, it is preferred that the strain concentration is measured using a tubidimeter according to a standard curve method.

BRIEF DESCRIPTION OF THE DRAWINGS

FIG. 1 is a graph that illustrates xylitol productivity with respect to time of fed-batch culture of *Candida tropicalis* cells in a chemical medium of the present invention;

FIG. 2 is a graph that illustrates xylitol productivity with respect to time of fed-batch culture of *Candida tropicalis* cells in a complex medium;

FIG. 3 is a graph that illustrates xylitol productivity with respect to time of recycling culture by centrifugation of *Candida tropicalis* cells primarily cultured in a chemical medium of the present invention;

FIG. 4 is a schematic diagram that illustrates an apparatus for producing xylitol in high yield by cell recycling according to a preferable embodiment of the present invention (bioreactor 10; peristaltic pump 20; microfiltration system 30; Hollow fiber membrane 32; suction pump 40; broth tank 50; blower 60; air inlet 11; air outlet 12, 31);

FIG. 5 is a graph that illustrates xylitol productivity with respect to time of recycling culture by vacuum microfiltration of *Candida tropicalis* cells primarily cultured in a chemical medium of the present invention;

FIG. 6 is a graph that illustrates xylitol productivity with respect to time of recycling culture by vacuum microfiltration of *Candida tropicalis* cells primarily cultured in a complex medium; and FIG. 7 is a graph that illustrates xylitol productivity with respect to time of recycling culture by pressurized microfiltration of *Candida tropicalis* cells primarily cultured in a chemical medium of the present invention.

MODES FOR CARRYING OUT THE INVENTION

Experimental Example

The concentrations of xylose and xylitol were measured using HPLC (Shimadzu C-R6A, Japan) refractive index detector (Shimadzu RID-6A, Japan) equipped with Sugar-Pak I column (Millipore, USA). At this time, water used as a solvent was allowed to flow at 70° C. at a rate of 0.6 Ml/min. Cell density was estimated by measuring turbidity at 600 nm using a tubidimeter and comparing the value to a previously prepared standard curve in which turbidity is related to cell dry weight. The concentration of dissolved oxygen was measured using a dissolved oxygen electrode (polarographic type, Ingold, Switzerland).

Example 1

Chemical Medium

Seed culture: the published *Candida tropicalis* KCTC 7221 cells were inoculated onto 50 Ml of a growth medium contained in a 250 Ml flask and cultured at 240 rpm and 30° C. for 10 hours.

Main culture: the seed culture was introduced and cultured in a 7 l fermenter (Biotron Ltd.) containing 2 l of a chemical medium composed of 150 g/l of xylose, 5 g/l of urea, 5 g/l of potassium diphosphate, 0.2 g/l of magnesium sulfate, metal salts (7 mg/l of $MnSO_4 \cdot 4H_2O$, 4 mg/l of $CoCl_2 \cdot 6H_2O$, 2 mg/l of $NaMoO_4 \cdot 2H_2O$, 2 mg/l of $ZnSO_4 \cdot 7H_2O$, 1 mg/l of $AlCl_3 \cdot 6H_2O$, 2 mg/l of $CuCl_2 \cdot 2H_2O$, 0.5 mg/l of $H_3BO_3$, 40 mg/l of $FeSO_4 \cdot 7H_2O$), and vitamins (5 mg/l of ascorbic acid, 10 mg/l of biotin, 25 mg/l of choline, 50 mg/l of folic acid, 10 mg/l of inositol, 25 mg/l of nicotinic acid, 1 mg/l of p-aminobenzoic acid, 5 mg/l of pantothenic acid, 1 mg/l of pyridoxine, 100 mg/l of riboflavin, 25 mg/l of thiamine). Fed-batch culture was performed in such a manner that during the fermentation, the fermentation medium was continuously supplemented with a 1 l solution containing 510 g xylose so that the volume of a final culture was maintained at 3 l, i.e., so that the total concentration of added xylose was maintained at 270 g/l. Fermentation conditions were as follows: agitation speed of 400 rpm, pH of 5.0 throughout the fermentation, fermentation temperature of 30° C., and aeration rate of 1.0 vvm. Xylitol productivity with respect to fermentation time was measured and the results are shown in FIG. 1. Referring to FIG. 1, 240 g/l of xylitol was obtained from 270 g/l of xylose after fermentation for 120 hours. As a result, the yield of xylitol to xylose was 89% and xylitol productivity was 2.0 g/l-h. These results show that for xylitol production, an inexpensive, chemically defined medium can be substituted for a conventional xylitol-producing medium.

Comparative Example 1

Complex Medium

Seed culture: the published *Candida tropicalis* KCTC 7221 cells were inoculated onto 50 Ml of a growth medium contained in a 250 Ml flask and cultured at 240 rpm and 30° C. for 10 hours.

Main culture: the seed culture was introduced and cultured in a 7 l fermenter containing 2 l of a complex medium composed of 150 g/l of xylose, 10 g/l of yeast extract, 5 g/l of potassium diphosphate, and 0.2 g/l of magnesium sulfate. Fed-batch culture was performed in such a manner that during the fermentation, the fermentation medium was continuously supplemented with a 1 l solution containing 510 g xylose so that the volume of a final culture was maintained at 3 l, i.e., so that the total concentration of added xylose was maintained at 270 g/l. Fermentation conditions were as follows: agitation speed of 400 rpm, pH of 5.0 throughout the fermentation, fermentation temperature of 30° C., and aeration rate of 1.0 vvm. Xylitol productivity with respect to fermentation time was measured and the results are shown in FIG. 2. Referring to FIG. 2, 230 g/l of xylitol was obtained from 270 g/l of xylose after fermentation for 108 hours. As a result, the yield of xylitol to xylose was 85% and xylitol productivity was 2.1 g/l-h.

Example 2

Cell Recycling Culture by Centrifugation

After culturing was performed in the same chemical medium as in Example 1 until immediately before xylose was depleted, the culture was centrifuged at 5,000 rpm for 20 minutes. The collected cells were inoculated onto 2 l of a fresh chemical medium and re-cultured. At this time, culture conditions were the same as in Example 1 and the concentrations of xylose and xylitol were measured in the same manner as in the above Experimental Example.

2 l of the primary culture before the centrifugation contained 218 g of xylitol. At this time, xylitol productivity was 2.3 g/l-h and the yield of xylitol to xylose was 74%. As a result of 14 recycling culture by the centrifugation, 3,076 g of xylitol was obtained from 28 l of whole culture and xylitol productivity and yield were respectively 5.4 g/l-h and 82% (see FIG. 3).

The production amount, productivity, and yield of xylitol after the 14 recycling culture by the centrifugation were respectively increased by 14 times, 2.4 times, and 8%, as compared to those of the primary culture.

From the above results, it can be seen that xylitol production efficiency by cell recycling of the present invention is much excellent, relative to that of a conventional batch culture.

Example 3

Cell Recycling Culture by Vacuum Microfiltration (Chemical Medium)

After culturing was performed in a bioreactor containing the same chemical medium as in Example 1 until immediately before xylose was depleted, the culture was transferred to a vacuum microfiltration system attached to the bioreactor to separate spent cells and a culture filtrate. The spent cells were recycled to the bioreactor containing 2 l of a fresh chemical medium and re-cultured. Culture conditions were the same as in Example 1 (see FIG. 4).

At this time, the vacuum microfiltration system was provided with hollow fiber membranes (0.45 μm in porosity, Mitsubishi Rayon, Japan) made of polyethylene. The hollow fiber membranes were attached to silicon tubes of both sides of the vacuum microfiltration system. Through the hollow fiber membranes, microfiltration was performed in a vacuum created by a pump. The concentration of xylitol was measured in the same manner as in the above Experimental Example.

2 l of the primary culture before the microfiltration contained 194 g of xylitol. At this time, xylitol productivity was 2.0 g/l-h and the yield of xylitol to xylose was 72%. As a result of eight recycling culture by the microfiltration, 2,026 g of xylitol was obtained from 16 l of whole culture and Xylitol productivity and yield were respectively 5.8 g/l-h and 87%. The production amount, productivity, and yield of xylitol after the eight recycling culture by the microfiltration were respectively increased by 10.4 times, 2.9 times, and 15%, as compared to those of the primary culture (see FIG. 5).

Comparative Example 2

Cell Recycling Culture by Vacuum Microfiltration (Complex Medium)

After culturing was performed in a bioreactor containing the same complex medium as in Comparative Example 1 under the same culture conditions as in Example 1 until immediately before xylose was depleted, the culture was transferred to a vacuum microfiltration system attached to the bioreactor to separate spent cells and a culture filtrate. The separated cells were recycled to the bioreactor containing 2 (of a fresh complex medium and re-cultured. At this time, the used vacuum microfiltration system was the same as that in Example 3.

2 l of the primary culture before the microfiltration contained 118 g of xylitol. At this time, xylitol productivity was 2.5 g/l-h and the yield of xylitol to xylose was 79%. As a result of seven recycling culture by the microfiltration, 972 g of xylitol was obtained from 14 l of whole culture and xylitol productivity and yield were respectively 5.4 g/l-h and 85%. The production amount, productivity, and yield of xylitol after the seven recycling culture by the microfiltration were respectively increased by 8.2 times, 2.2 times, and 6%, as compared to those of the primary culture (see FIG. 6).

From the comparison results of Example 3 and Comparative Example 2, it can be seen that a chemical medium is more suitable for recycling culture than a complex medium.

Comparative Example 3

Cell Recycling Culture by Pressurized Microfiltration (Chemical Medium)

After culturing was performed in the same chemical medium and culture conditions as in Example 1 until immediately before xylose was depleted, spent cells and a culture filtrate were separated in the same manner as in Example 3 using a pressurized microfiltration system (0.65 μm in porosity, Amersham Biosciences, CFP-6-D-4MA). The spent cells were recycled, and the culture filtrate was recovered to measure the concentration of xylitol in the culture filtrate.

As shown in FIG. 7, 2 l of the primary culture before the microfiltration contained 110 g of xylitol. At this time, xylitol productivity was 2.3 g/l-h and the yield of xylitol to xylose was 73%. As a result of two recycling culture by the microfiltration, 179 g of xylitol was obtained from 4 l of whole culture and xylitol productivity and yield were respectively 2.7 g/l-h and 60%. The production amount and productivity of xylitol after the two recycling culture by the microfiltration were respectively increased by 1.6 times and 1.2 times but xylitol yield was reduced by 13%, as compared to those of the primary culture.

From the above results, it is judged that some of the cells were broken by pressure in the pressurized microfiltration system.

Example 4

Culturing was performed in the same culture conditions and medium as in Example 1 while varying the volume of the culture medium within the range of 2-5 l. The cells were concentrated to different densities in a vacuum microfiltration system and then recycled.

The concentrated cells were inoculated onto fresh chemical media (2 l for each) and again cultured for 8 hours. Total productivity and specific productivity of xylitol according to cell density were measured and the results are summarized in Table 1 below.

At this time, the total productivity of xylitol was calculated by dividing the concentration of xylitol accumulated for 8 hours by 8 hours and the specific productivity of xylitol was calculated by dividing the total productivity by the density of the cells used.

As a result, when cell density was 35 g/l, the most excellent results were obtained in terms of xylitol productivity (10.2 g/l-h) and yield (85%).

TABLE 1

| Cell density (g/l) | Yield (%) | Total productivity of xylitol (g/l-h) | Specific productivity of xylitol (g/g-h) |
|---|---|---|---|
| 10 | 85 | 3.4 | 0.34 |
| 15 | 87 | 5.0 | 0.33 |
| 20 | 88 | 6.4 | 0.32 |
| 25 | 88 | 8.0 | 0.32 |
| 30 | 87 | 9.4 | 0.31 |
| 35 | 86 | 10.2 | 0.29 |
| 40 | 82 | 9.3 | 0.23 |
| 50 | 78 | 8.0 | 0.16 |
| Batch culture (control) | 76 | 2.0 | 0.33 |

From Table 1, it can be seen that recycling culture of concentrated cells by vacuum microfiltration can provide 5-fold higher xylitol productivity and 10% higher xylitol yield, relative to a common culture that produces 97 g/l of xylitol for 48 hours on an average (total productivity of 2.0 g/l-h).

INDUSTRIAL APPLICABILITY

As apparent from the above description, the present invention provides a process for continuously producing xylitol from xylose in high yield by culturing a microbial strain in a chemically defined medium, concentrating the strain in a vacuum microfiltration bioreactor or a centrifuge, and recycling the concentrated strain.

Therefore, the production process of the present invention can be applied to an automated production system and a cost incurred for preparative procedures before culturing can be diminished, unlike a common fermentation process, thereby enabling large-scale production of inexpensive xylitol.

What is claimed is:

1. A process for producing xylitol in high yield by recycling culture of a strain of the genus *Candida*, which comprises the steps of:
    inoculating the strain in a xylose-containing medium and culturing the strain in the xylose-containing medium in a bioreactor;
    releasing a culture from the bioreactor and introducing a fresh xylose-containing medium to the bioreactor continuously;
    separating the strain and a culture filtrate from the culture, which is performed by a vacuum microfiltration system or a centrifuge; and
    recycling the strain to the bioreactor and recovering xylitol from the culture filtrate wherein the xylose-containing medium is a chemically defined medium that comprises 5-300 g/l of xylose, 1-10 g/l of urea, 1-10g/l of potassium diphosphate, 0.01-1 g/l of magnesium sulfate, 0.1-10 mg/l of $MnSO_4.4H_2O$, 0.1-10 mg/l of $CoCl_2.6H_2O$, 0.1-10 mg/l of $NaMoO_4.2H_2O$, 0.1-10 mg/l of $ZnSO_4.7H_2O$, 0.1-10 mg/l of $AlCl_3.6H_2O$, 0.1-10 mg/l of $CuCl_2.2H_2O$, 0.01-5 mg/l of $H_3BO_3$, 1-100 mg/l of $FeSO_4.7H_2O$, 0.1-10 mg/l of ascorbic acid, 1-100 mg/l of biotin, 1-100 mg/l of choline, and 0.1-10mg/l of pyridoxine, or a complex medium.

2. The process of claim 1, wherein the strain of the genus *Candida* is *Candida tropicalis* or its mutant strain.

3. The process of claim 1, wherein the culturing is performed by a fed-batch culture or a batch culture.

4. The process of claim 3, wherein in the fed-batch culture, the medium is gradually supplemented with xylose so that the concentration of xylose is maintained at 40-50 g/l on the basis of the medium.

5. The process of claim 1, wherein the culturing is performed at an agitation speed of 400-600 rpm.

6. The process of claim 1, wherein the separated strain is concentrated to a density of 10-100 g/l and recycled.

7. The process of claim 3, wherein the culturing is performed at an agitation speed of 400-600 rpm.

8. The process of claim 4, wherein the culturing is performed at an agitation speed of 400-600 rpm.

9. A process for producing xylitol in high yield by recycling culture of a strain of the genus *Candida*, which comprises the steps of:
    inoculating the strain in a xylose-containing medium and culturing the strain in the xylose-containing medium in a bioreactor;

releasing a culture from the bioreactor and introducing a fresh xylose-containing medium to the bioreactor continuously;

separating the strain and a culture filtrate from the culture; and recycling the strain to the bioreactor and recovering xylitol from the culture filtrate wherein the xylose-containing medium is a chemically defined medium that comprises 5-300 g/l of xylose, 1-10 g/l of urea, 1-10 g/l of potassium diphosphate, 0.01-1 g/l of magnesium sulfate, 0.1-10 mg/l of $MnSO_4.4H_2O$, 0.1-10 mg/l of $CoCl_2.6H_2O$, 0.1-10 mg/l of $NaMoO_4.2H_2O$, 0.1-10 mg/l of $ZnSO_4.7H_2O$, 0.1-10 mg/l of $AlCl_3.6H_2O$, 0.1-10 mg/l of $CuCl_2.2H_2O$, 0.01-5 mg/l of $H_3BO_3$, 1-100 mg/l of $FeSO_4.7H_2O$, 0.1-10 mg/l of ascorbic acid, 1-100 mg/l of biotin, 1-100 mg/l of choline, and 0.1-10 mg/l of pyridoxine.

10. The process of claim 9, wherein the culturing is performed by a fed-batch culture or a batch culture.

11. The process of claim 10, wherein in the fed-batch culture, the medium is gradually supplemented with xylose so that the concentration of xylose is maintained at 40-50 g/l on the basis of the medium.

12. The process of claim 9, wherein the culturing is performed at an agitation speed of 400-600 rpm.

13. The process of claim 9, wherein the separation of the strain and the culture filtrate from the culture is performed by a vacuum microfiltration system or a centrifuge.

14. The process of claim 9, wherein the separated strain is concentrated to a density of 10-100 g/l and recycled.

15. The process of claim 10, wherein the culturing is performed at an agitation speed of 400-600 rpm.

16. The process of claim 11, wherein the culturing is performed at an agitation speed of 400-600 rpm.

17. The process of claim 14, wherein the culturing is performed at an agitation speed of 400-600 rpm.

* * * * *